United States Patent
Glenn

(10) Patent No.: US 7,608,065 B2
(45) Date of Patent: *Oct. 27, 2009

(54) BONE SUPPORTED VASCULAR ACCESS PORT

(76) Inventor: Bradley J. Glenn, 1136 Pleasant Valley Dr., Oneida, WI (US) 54155

(*) Notice: Subject to any disclaimer, the term of this patent is extended or adjusted under 35 U.S.C. 154(b) by 0 days.

This patent is subject to a terminal disclaimer.

(21) Appl. No.: 11/700,320

(22) Filed: Jan. 30, 2007

(65) Prior Publication Data

US 2007/0179456 A1 Aug. 2, 2007

Related U.S. Application Data

(60) Provisional application No. 60/762,848, filed on Jan. 30, 2006.

(51) Int. Cl.
*A61M 37/00* (2006.01)

(52) U.S. Cl. .................. 604/288.02; 604/288.01; 604/288.04; 604/175; 604/174

(58) Field of Classification Search ..................
604/288.01–288.04, 890.1, 175, 19, 48, 604/502, 93.01, 174
See application file for complete search history.

(56) References Cited

U.S. PATENT DOCUMENTS

| | | | |
|---|---|---|---|
| 3,397,699 A | 8/1968 | Kohl |
| 3,692,029 A | 9/1972 | Adair |
| 3,713,447 A | 1/1973 | Adair |
| 3,938,530 A | 2/1976 | Santomieri |
| 3,951,147 A | 4/1976 | Tucker |
| 4,043,338 A | 8/1977 | Homm |
| 4,077,412 A | 3/1978 | Moossun |
| 4,543,088 A | 9/1985 | Bootman |
| 4,569,675 A | 2/1986 | Prosl |
| 4,608,965 A | 9/1986 | Anspach, Jr. |
| 4,627,838 A | 12/1986 | Cross |
| 4,673,394 A | 6/1987 | Fenton, Jr. |
| 4,704,103 A | 11/1987 | Stober |
| 4,743,231 A | 5/1988 | Kay |
| 4,772,270 A | 9/1988 | Wiita |
| 4,778,452 A | 10/1988 | Moden |
| 4,802,885 A | 2/1989 | Weeks |
| 4,880,414 A | 11/1989 | Whipple |
| 4,995,868 A | 2/1991 | Brazier |
| 5,108,377 A | 4/1992 | Cone |
| 5,112,310 A | 5/1992 | Grobe |
| 5,113,846 A | 5/1992 | Hiltebrandt |
| 5,167,638 A | 12/1992 | Felix |
| 5,215,103 A | 6/1993 | Desai |
| 5,217,451 A | 6/1993 | Freitas |

(Continued)

*Primary Examiner*—Kevin C Sirmons
*Assistant Examiner*—Laura C Schell
(74) *Attorney, Agent, or Firm*—Heisler & Associates

(57) ABSTRACT

A vascular access port is disclosed for subcutaneous implantation. The port is particularly adapted to be affixed to a bone to securely hold the port in position, to assist medical personnel in finding the port and to decrease a visibility of the port. The port has a chamber therein which is accessed by a needle through a septum adjacent the chamber. The chamber is placed into fluid communication with the vascular structure of the patient, such as through catheter tubing. The chamber is surrounded by a body with an outer surface which is preferably fitted with threads to facilitate secure but removable attachment of the port within a hole in the bone where the port is to be implanted.

10 Claims, 2 Drawing Sheets

U.S. PATENT DOCUMENTS

| | | | |
|---|---|---|---|
| 5,275,610 A | 1/1994 | Eberbach | |
| 5,306,226 A | 4/1994 | Salama | |
| 5,332,398 A * | 7/1994 | Miller et al. | 604/175 |
| 5,338,297 A | 8/1994 | Kocur | |
| 5,344,439 A | 9/1994 | Otten | |
| 5,356,382 A | 10/1994 | Picha | |
| 5,360,407 A | 11/1994 | Leonard | |
| 5,365,926 A | 11/1994 | Desai | |
| 5,387,192 A | 2/1995 | Glantz | |
| 5,399,168 A | 3/1995 | Wadsworth, Jr. | |
| 5,421,832 A | 6/1995 | Lefebvre | |
| 5,443,449 A | 8/1995 | Buelna | |
| 5,454,365 A | 10/1995 | Bonutti | |
| 5,527,336 A | 6/1996 | Rosenbluth | |
| 5,562,618 A | 10/1996 | Cai | |
| 5,624,395 A | 4/1997 | Mikhail | |
| 5,624,399 A | 4/1997 | Ackerman | |
| 5,833,654 A | 11/1998 | Powers | |
| 5,848,989 A * | 12/1998 | Villani | 604/288.02 |
| 5,954,687 A * | 9/1999 | Baudino | 604/48 |
| 5,957,900 A | 9/1999 | Ouchi | |
| 5,971,954 A | 10/1999 | Conway | |
| 5,989,216 A | 11/1999 | Johnson | |
| 5,990,382 A * | 11/1999 | Fox | 623/16.11 |
| 6,080,142 A | 6/2000 | Sachse | |
| 6,099,506 A | 8/2000 | Macoviak | |
| 6,190,352 B1 | 2/2001 | Haarala | |
| 6,213,973 B1 | 4/2001 | Eliasen | |
| 6,228,088 B1 * | 5/2001 | Miller et al. | 606/80 |
| 6,355,020 B1 | 3/2002 | Bousquet | |
| 6,569,150 B2 | 5/2003 | Teague | |
| 6,572,587 B2 | 6/2003 | Lerman | |
| 6,623,448 B2 | 9/2003 | Slater | |
| 6,629,953 B1 | 10/2003 | Boyd | |
| 6,629,956 B1 | 10/2003 | Polidoro | |
| 6,699,216 B2 | 3/2004 | Ikeguchi | |
| 6,758,831 B2 | 7/2004 | Ryan | |
| 6,780,175 B1 | 8/2004 | Sachdeva | |
| 6,997,885 B2 | 2/2006 | Lubock | |
| 6,997,909 B2 | 2/2006 | Goldberg | |
| 6,997,914 B2 | 2/2006 | Smith | |
| 7,037,321 B2 | 5/2006 | Sachdeva | |
| 2001/0049492 A1 | 12/2001 | Frazier | |
| 2002/0165553 A1 | 11/2002 | Elbert | |
| 2002/0177806 A1 | 11/2002 | Meier | |
| 2003/0014009 A1 | 1/2003 | Kletschka | |
| 2004/0078004 A1 | 4/2004 | Bourne | |
| 2004/0249342 A1 | 12/2004 | Khosravi | |
| 2004/0254537 A1 | 12/2004 | Conlon | |
| 2005/0043735 A1 | 2/2005 | Ahmad | |
| 2005/0075644 A1 | 4/2005 | DiPoto | |
| 2005/0113929 A1 | 5/2005 | Cragg | |
| 2005/0119617 A1 | 6/2005 | Stecker | |
| 2005/0131383 A1 | 6/2005 | Chen | |
| 2005/0177105 A1 | 8/2005 | Shalev | |
| 2005/0251168 A1 | 11/2005 | Hess | |
| 2007/0088258 A1 | 4/2007 | Wenchell | |
| 2007/0088259 A1 | 4/2007 | Chu | |
| 2007/0276493 A1 | 11/2007 | Malandain | |

* cited by examiner

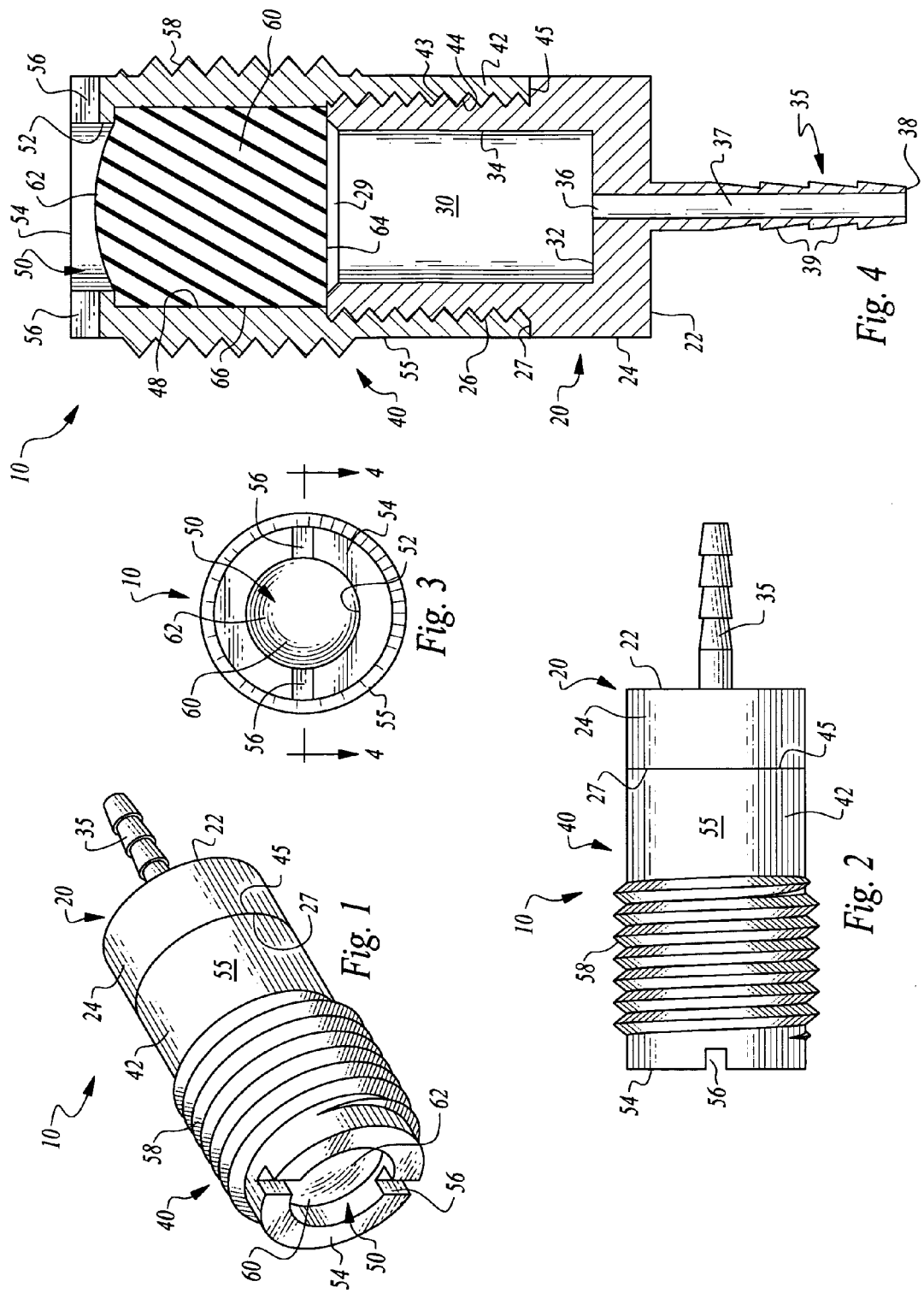

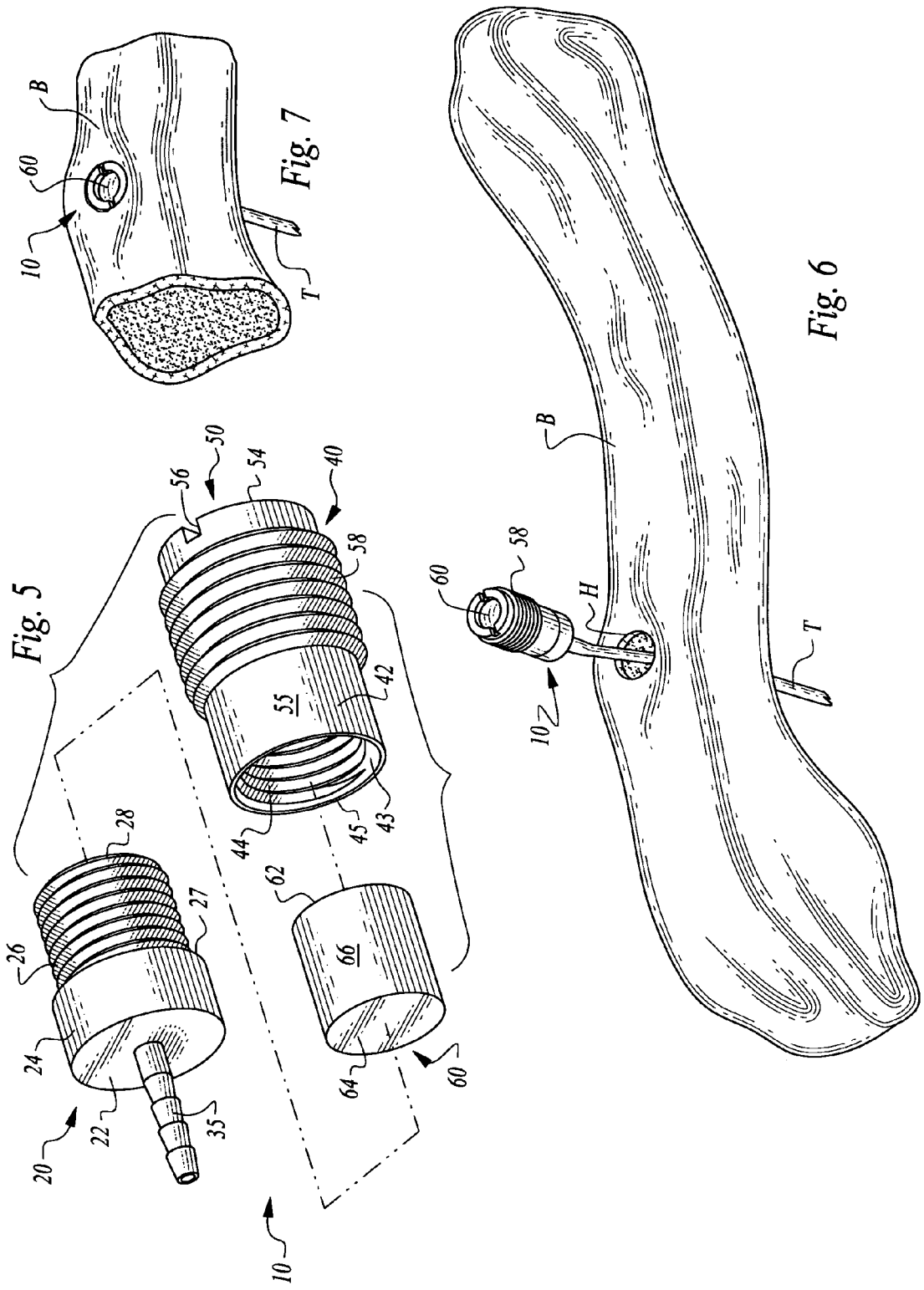

BONE SUPPORTED VASCULAR ACCESS PORT

CROSS-REFERENCE TO RELATED APPLICATIONS

This application claims benefit under Title 35, United States Code §119(e) of U.S. Provisional Application No. 60/762,848 filed on Jan. 30, 2006.

FIELD OF THE INVENTION

The following invention relates to implantable vascular access ports for implantation subcutaneously and which can receive a medication or other liquid preparation by a needle inserted through the skin and into the port, and then on into the vascular system of the patient. More particularly, this invention relates to subcutaneous implantable vascular access ports which are particularly configured to be affixed to a bone or other subcutaneous structure to provide secure placement of the access port.

BACKGROUND OF THE INVENTION

Subcutaneously implanted vascular access devices, or ports, have been used for many years to provide long term vascular access in patients that require frequent or periodic therapeutic infusions or blood draws. Prior art ports generally have a body which contains a chamber accessible by a self-sealing septum and an outlet which is connected to a catheter which interfaces with the vascular system. The base of the port is a generally flat side of the port which is intended to lie against the body, so the septum is generally oriented toward the skin surface. Many variations are possible. The septum may be convex or concave. The body may be plastic, metal or a combination of materials. The septum may be directly opposite the base, or may be angled relative to the base.

In current practice, the port is implanted into a subcutaneous pocket during a minor surgical procedure. One limitation to the development of smaller profile ports is the problem of port stability within the body after being placed. Ports in use currently have a propensity to flip-over within the body if not sutured in place, rendering them inaccessible because the septum is facing down rather than up. The smaller the port, the greater the propensity to flip-over, and the harder it is to suture the port in place due to the smaller incision and smaller working pocket within which to suture. While suturing can be somewhat effective, it is time consuming and not entirely reliable. Thus, there is a need for a method to increase port stability while minimizing port implantation profile.

One such prior art port with a body that exhibits a generally elongate form and with an associated elongate septum is described in U.S. Pat. No. 6,213,973. While such a configuration does allow for a slightly minimized incision size, this prior art access port is not stabilized and is thus susceptible to "flipping-over" or otherwise rotating into an undesirable position.

Accordingly, a need exists for a vascular access port which provides both the benefit of stability once implanted and a small profile for insertion through a small incision, with the vascular access port being sufficiently small to allow for a minimization of size of the access port and other negative attributes associated with provision of such a vascular access port for the patient.

Another problem with prior art implantable subcutaneous vascular access ports is that in patients with low body fat, the vascular access port is often highly visible as a protrusion beneath the skin. Such appearance is often considered to be particularly undesirable. In other patients, it can be difficult to find the vascular access port due to the particular patient's physiology tending to excessively disguise the location of the vascular access port. With this invention, the port is fixed in a reliable position which is neither too obvious to the casual observer, nor too difficult to find. Furthermore, with this invention the port is fixed securely in position so that no concern for displacement of the port is presented.

SUMMARY OF THE INVENTION

A subcutaneous implantable vascular access port is provided according to this invention which is particularly adapted to be affixed to a bone of the patient. For instance, the port could be configured to be coupled to the clavicle of the patient. Initially, a hole is formed in the bone at the implantation site for the port. The port is configured so that it can be placed within this hole in the bone and held securely within the hole in the bone. For instance, an outer surface of the port can be fitted with a series of threads which engage sides of the hole in the bone to secure the port to the bone. Such threads can both support the port during implantation and also facilitate removal of the port when it is no longer needed.

The port preferably includes a chamber contained within a body forming the port. An aperture passes through the body and provides access into the chamber for a needle. A septum is interposed between the aperture and the chamber. This septum is formed of a silicone material or other resilient material which can be penetrated by a needle and reseal after removal of the needle. Preferably, the body is formed in two parts including a base portion and a collar portion with the septum interposed between the collar portion and the base portion and with the chamber formed primarily within the base portion. The entire body is preferably substantially cylindrical to facilitate its fitting securely within a cylindrical hole passing through the bone.

An extension preferably extends down from a lower surface of the base with an outlet connecting the chamber to the extension. Catheter tubing can be attached to the extension with the tubing extending to a vein or other vascular structure where fluid communication between the vascular structure of the chamber is provided. Particular details of such vascular interface are described in more detail in U.S. patent application Ser. No. 11/651,770, incorporated herein by reference in its entirety.

The hole typically passes entirely through the bone so that the extension and tubing extend out one end of the hole in the bone with the septum being accessible adjacent an opposite end of the hole in the bone. Because the port is primarily within a bone, such as the clavicle, the port does not present an unsightly appearance, but rather is substantially completely concealed within the bone. On the other hand, a medical professional can palpitate the clavicle of the patient and easily feel a slight depression defined by the hole in the bone and the aperture in the body of the port or a slight rise caused by the septum. A medical professional can then utilize a needle to access the chamber through the septum and through the skin of the patient.

OBJECTS OF THE INVENTION

Accordingly, a primary object of the present invention is to provide a subcutaneous vascular access port which facilitates introduction of a fluid preparation into the bloodstream of a patient in a reliable and repeatable fashion.

Another object of the present invention is to provide a vascular access port which is held securely in position subcutaneously.

Another object of the present invention is to provide a vascular access port which is easy for a medical professional to use.

Another object of the present invention is to provide a vascular access port which is affixed to a bone to allow the vascular access port to be securely held in place.

Another object of the present invention is to provide a vascular access port which is substantially invisible to a casual observer.

Another object of the present invention is to provide a vascular access port which can be readily found by a medical professional.

Another object of the present invention is to provide a vascular access port which is easy to implant in a secure fashion and which then can be repeatedly utilized for injection of medications or other preparations into the bloodstream of a patient or to draw blood.

Another object of the present invention is to provide a method for affixing a port subcutaneously with vascular access provided by the port.

Other further objects of the present invention will become apparent from a careful reading of the included drawing figures, the claims and detailed description of the invention.

BRIEF DESCRIPTION OF THE DRAWINGS

FIG. 1 is a perspective view of the subcutaneous vascular access port of this invention according to a preferred embodiment.

FIG. 2 is a side elevation view of that which is shown in FIG. 1.

FIG. 3 is an end elevation view of that which is shown in FIG. 1.

FIG. 4 is a full sectional view of that which is shown in FIG. 1.

FIG. 5 is an exploded parts view of that which is shown in FIG. 1.

FIG. 6 is a perspective view of the vascular access port of this invention along with tubing and shown adjacent to a hole in a bone during the process of implanting the vascular access port into the hole in the bone, for secure positioning of the vascular access port subcutaneously within a patient.

FIG. 7 is a perspective view similar to that which is shown in FIG. 6, but after completion of the implantation procedure.

DESCRIPTION OF THE PREFERRED EMBODIMENT

Referring to the drawings, wherein like reference numerals represent like parts throughout the various drawing figures, reference numeral 10 is directed to a bone supported vascular access port (FIGS. 6 and 7). The port 10 is configured with an outer surface 55 (FIG. 1) which can fit within a hole H in a bone B to secure the port 10 in fixed position subcutaneously within the patient. Catheter tubing T is coupled to the port 10 for vascular access between a chamber 30 (FIG. 4) within the port 10, and into the vascular system of the patient. An aperture 50 (FIGS. 1 and 4) provides access to the chamber 30 through a septum 60 which allows a needle to pass therethrough and which can reseal multiple times after needle removal. The port 10 thus provides a securely positioned, easily findable and usable subcutaneous vascular access port which also is substantially invisible to a casual observer of the patient.

In essence, and with particular reference to FIGS. 1 and 4, basic details of the port 10 of this invention are described according to a preferred embodiment. The port 10 is generally formed as a rigid body surrounding a chamber 30. This rigid body is preferably formed of two separate rigid portions including a base 20 and a collar 40. The chamber 30 is preferably formed primarily within the base 20. The collar 40 is configured to be attachable, preferably permanently, to the base 20.

The collar 40 includes an aperture 50 therein through which a needle can pass, so that the needle can pass entirely through the collar 40 and into the chamber 30. A septum 60 is interposed between the collar 40 and the base 20 so that the septum 60 is adjacent the chamber 30, with the septum 60 preferably substantially entirely within the collar 40. The base 20 and collar 40 preferably are attached together with a space therebetween slightly less than a size of the septum 60 so that the septum 60 is compressed somewhat between the base 20 and the collar 40.

An extension 35 extends from the base 20 and provides fluid access between the chamber 30 and tubing T, which can extend to and interface with the vascular system of the patient. The collar 40 includes an outer surface 55 which is configured to abut sides of a hole H in a bone B into which the port 10 is to be affixed. This outer surface 55 is preferably formed with bone engagement threads thereon so that the port 10 is threaded into the hole H in the bone B for secure but removable attachment of the port 10 to the bone B.

More specifically, and with particular reference to FIGS. 4 and 5, particular details of the base 20 are described according to a preferred embodiment. The base 20 is preferably configured as only a portion of a body forming the port 10. The body of the port 10 is generally defined as a rigid portion of the port 10 which surrounds and defines the chamber 30, other than where the aperture 50 provides access into the chamber 30. In this preferred embodiment, the base 20 defines a lower portion of this body forming the port 10.

The base 20 is preferably a rigid unitary mass of biocompatible metal, such as stainless steel. The base 20 could alternatively be formed of biocompatible plastic materials or other biocompatible materials. The base 20 is preferably generally symmetrical about a central axis and exhibits a generally hollow cylindrical form. In particular, the base 20 includes a lower wall 22 preferably substantially perpendicular to a central axis of the base 20 and port 10. A side wall 24 extends perpendicularly from the lower wall 22, with the side wall 24 preferably being substantially cylindrical.

Male threads 26 preferably extend from this side wall 24. These male threads 26 are preferably only provided adjacent an upper end 28 of the side walls 24. The male threads 26 end at a stop 26 where an outer diameter of the side wall 24 transitions from a greater diameter adjacent the lower wall 22, to a lesser diameter adjacent the upper end 28 and with the male threads 26 thereon. In this way, female threads 44 on the collar 40 can engage with the male threads 26 of the base 20 and allow portions of the side wall 24 of the base 20 to be flush with the outer surface 55 of the collar 40 (described in detail below).

The upper end 28 of the base 20 is open with preferably a bevel 29 defining a transition from the upper end 28 into the chamber 30. The chamber 30 defines a hollow cylindrical interior of the base 20 in the preferred embodiment. The chamber 30 could in fact have a variety of different shapes, sizes or configurations, with a cylindrical form being most preferred. The chamber 30 is substantially enclosed on all sides by the base 20 other than adjacent the bevel 29 and upper end 28 of the base 20 where the chamber 30 is preferably entirely open.

The chamber 30 includes a floor 32 which is preferably substantially perpendicular to the central axis of the base 20, with the floor 32 preferably substantially circular in shape and parallel with the lower wall 22. Sides 34 of the chamber 30 extend perpendicularly up from the floor 32 to the upper end 28 of the base 20.

An extension 35 extends from the lower end 22 of the base 20. This extension 35 extends downwardly and includes a conduit 37 therein so that the extension 35 is hollow. An outlet 36 provides for fluid communication between the chamber 30 and the conduit 37 within the extension 35. The extension 35 extends to a tip 38. Barbs 39 are preferably formed on an outer surface of the extension 35. The extension 35 can have catheter tubing T slipped over an outer surface thereof with the barbs 39 tending to keep the tubing on the extension. As an alternative, ribs could be provided on the extension for securing of the tubing T, either with or without separate clamping structures, such as described in attachment of tubing to the vascular access port described in U.S. patent application Ser. No. 11/651,770, incorporated herein by reference. The extension 35 provides a preferred form of a means to secure the chamber 30 to a vascular structure of the patient and to provide for fluid communication between the chamber 30 and the vascular system of the patient, along with the catheter tubing T.

The extension 35 and outlet 36 are shown axially aligned with the central axis of the base 20, port 10 and chamber 30. Most preferably, this outlet 36 is offset at least slightly from this centerline, and possibly formed to extend at an angle to the central axis. The outlet 36 could alternatively be jogged or stepped so that it does not provide a purely straight axial form extending along a centerline of the port 10. By offsetting the outlet 36, the possibility that a needle passing through the aperture 50 and through the septum 60, and into the chamber 30 might possibly also pass through the outlet 36 and somehow damage the tubing T is precluded. Other techniques for avoiding inserting a needle too far and all the way through the port 10 include providing a stop on the needle so that the needle cannot be inserted too deeply or moving the outlet 36 so that it extends through one of the sides 34 of the chamber 30, rather than the floor 32 of the chamber 30.

With particular reference to FIGS. 4 and 5, particular details of the collar 40 of this invention are described. The collar 40 preferably defines a portion of the body of the port 10 surrounding the chamber 30. Thus, in this preferred embodiment the base 20 and collar 40 together define the body of the port 10. As an alternative, the body could be a single unitary mass of material and the septum 60 could be compressed and put into place through the aperture 50.

The collar 40 is preferably a substantially cylindrical rigid unitary mass of material preferably formed of a common material with the base 20, such as a biocompatible stainless steel. Other biocompatible materials could also be utilized for the base 20 and collar 40. The collar 40 is generally ring-like in form so that the collar 40 is open on either end thereof.

The collar 40 includes a lower ring 42 defining a portion of the collar 40 which overlaps a portion of the base 20. This lower ring 42 has an inner surface 43 which preferably has female threads 44 thereon. The female threads 44 are sized to be complemental with the male threads 26 of the base 20 so that the collar 40 can be threaded onto the base 20. A rim 45 defines a lowermost portion of the lower ring 42 of the collar 40. This rim 45 preferably abuts the stop 27 of the base 20 when the collar 40 has been entirely fitted upon the base 20.

A compartment is formed within the collar 40 between the lower ring 42 and the aperture 50. This compartment is sized to receive the septum 60 therein so that the septum 60 is adjacent the chamber 30 and generally interposed between the aperture 50 and the chamber 30. This compartment is preferably defined by a cylindrical wall 48 within the collar 40. Dimensions of the compartment, and particularly a length between the rim 45 and the aperture 50 is preferably less than a length of the septum 60 from a top 62 to a bottom 64. In this way, the septum 60 is slightly compressed between the aperture 50 and the stop 27 of the base 20, so that the septum 60 is pre-compressed within the port 10. Such pre-compression can assist the septum 60 in most effectively resealing after penetration by a needle and removal of that needle.

The collar 40 preferably supports the aperture 50 at an end of the collar 40 most distant from the base 20 and an end of the port 10 opposite the extension 35 or other outlet from the chamber 30. This aperture 50 defines an opening through which a needle is passed to penetrate the septum 60 and pass into the chamber 30.

The aperture 50 preferably includes a lip 52 which has a slightly lesser diameter than a diameter of the cylindrical wall 48 of the compartment within the collar 40. Thus, the lip 52 helps to keep the septum 60 from translating linearly along a central axis of the port 10 and out of the aperture 50. A face 54 defines an inwardly extending surface surrounding the aperture 50 and facing upwardly generally perpendicular to the central axis. This face 54 includes at least one slot 56 therein and preferably a pair of slots 56 on opposite sides of the aperture 50. These slots 56 can receive a torque applying tool, such as a screwdriver type tool. In this way, such a tool can be utilized to thread the entire port 10 into the hole H in the bone B for both insertion and removal of the port 10.

An outer surface 55 of the collar 40 extends from the face 54 down to the rim 45. This outer surface 55 is preferably substantially cylindrical in form, but could have a variety of different forms. The outer surface 55 preferably supports a bone engagement surface configured as a means to fasten the port 10 to a bone B. Most preferably, this fastening means includes bone threads 58 thereon. These bone threads 58 can thread into sides of the hole H in the bone B to secure the port 10 to the bone B. The threads 58 can both be used to hold the port 10 securely in place and also allow the port 10 to be drawn more deeply into the hole H or be removed out of the hole H, depending on the positioning desires of the medical professional implanting the port 10.

These bone threads 58 can be formed to be self-tapping so that they can be placed into a hole H which is not yet threaded. Alternatively, a tapping tool can be utilized to tap threads into the hole H in the bone B before insertion of the port 10 into the hole H in the bone B.

As an another alternative, the outer surface 55 could merely be provided with a roughened surface and a close tolerance for friction fit to be provided between the outer surface 55 and the hole H, so that the port 10 is securely held within the hole H and the bone B. If desired, the outer surface 55 can be roughened or ribbed axially or circumferentially, or in other orientations, so that re-ossification and bone ingrowth to further secure the port 10 within the hole H in the bone B is further facilitated with or without the threads 58. With such re-ossification, the port 10 can also add strength back to the bone B which might have been reduced in strength due to placement of the hole H in the bone B.

Other fastening means for the port could include clasps, such as those used to hold stud earrings, with a fastener below the hole H in the bone B adapted to be coupled to the port. The port outer surface could include a radially expanding structure to engage and secure to the bone B. The outer surface 55 could be barbed with fixed or movable barbs. A rivet type tool could be configured to hold the port in place or adhesive could be utilized. Such fastening means could be used alone or in combination.

The septum 60 is preferably a solid mass of biocompatible silicone material. This material is preferably slightly resilient and able to be penetrated by a needle and has the particular property of being able to reseal after the needle has penetrated the septum 60 and then has been later removed. The septum 60 is preferably placed in compression to further enhance this resealing feature of the septum 60. The septum 60 preferably has a cylindrical form with a top 62 opposite a bottom 64 with both the top 62 and bottom 64 both being round in shape. A perimeter 66 defines a cylindrical wall extending from the top 62 to the bottom 64. While the septum 60 is preferably cylindrical, if the compartment within the collar 40 has a different geometric configuration, the septum 60 could be appropriately modified to fit modifications to the compartment within the collar 40. Because the septum 60 is pre-compressed somewhat, portions of the top 62 and bottom 64 bulge out of the aperture 50 and into the chamber 30.

In use and operation, and with particular reference to FIGS. 6 and 7, particular details of the method of using the port 10 of this invention are described, according to a preferred embodiment. When a patient is to have the port 10 implanted, the medical professional first identifies a bone B into which the port 10 is to be implanted. Most typically in a preferred embodiment of this invention, the bone B to be utilized is the clavicle with the intention of coupling catheter tubing T between the port 10 and one of the carotid veins of the patient.

The medical professional identifies the desired location within the clavicle for implantation of the port 10. The medical professional then provides an appropriate incision adjacent the clavicle and utilizes an appropriate hole forming tool to form the hole H within the bone B of the patient. This hole H can be later tapped with threads or the port 10 can be provided with bone threads 58 which are sufficiently self-tapping in nature so that the port 10 can be placed into the hole H in threading fashion. A torque applying tool, such as some form of tool screwdriver is caused to interface with the slots 58 in the face 54 of the collar 40 on the port 10 and the port 10 is placed into the hole H and then rotated until it has been located entirely down into the hole H (FIG. 7).

Because the hole H passes entirely through the bone B and the tube T has first been placed upon the port 10 and extended through the hole H, the tube T now extends out a lower side of the bone B and is ready for a secondary medical procedure to provide vascular access between the tubing T and the particular vein or other vascular structure, where interface with the bloodstream of the patient is to occur.

When a medical professional later needs to provide a dose of a medical preparation into the bloodstream of the patient, or draw blood, the medical professional first palpitates the clavicle to identify the depression or rise formed by the hole H and/or the aperture 50 in the face 54 of the collar 40 or the septum 60 of the port 10. Once this depression or rise has been found by such palpitation, the medical professional can align a needle with this location and insert the needle through the skin and through the septum 60 and into chamber 30 of the port 10. A syringe or other appropriate device coupled to the needle is then utilized to pass the liquid preparation through the needle and into the chamber 30. This preparation can then pass on into the bloodstream through the tubing T.

The medical professional can then remove the needle allowing the septum 60 to reseal. This procedure can be repeated numerous times before the septum 60 wears out. At which time, the port 10 can be optionally replaced.

When the port 10 is no longer needed, a surgeon will access the port 10 in a minor surgical procedure and utilize a torque applying tool coupled to the slots 56 to rotate the port 10. Such rotation in the proper direction will cause the port 10 to rotate and translate out of the hole H. The point of vascular access can also be appropriately repaired and the port 10 entirely removed. If desired, bone ingrowth media can be packed into the hole H before closing an incision through which the medical procedure is performed, to promote bone B regrowth to fill in the hole H.

While the hole H is shown as a complete hole passing entirely through the bone B, it is conceivable that the hole H could pass through a side of the bone B so that it is not entirely surrounded by bone, but is only partially surrounded by bone B. If such bone surrounding nature for the hole H and the bone B is greater than half of a complete circle, the port 10 can still be securely held therein. Also, a bracket could provide at least a portion of the fastening means and fasten the port 10 to the bone B without any hole through the bone B. Such a bracket could clamp to the bone B or use a fastener (i.e. a screw) penetrating the bone B to secure the bracket to the bone B, with the bracket formed with or securely coupleable to the port 10. While the hole H is preferably circular in cross-section and cylindrical in form, it is conceivable that this hole H could have a square cross-section or some other cross-section. The port 10 could be formed to have a complemental cross-section with the hole H or the hole H and port 10 could have different shapes, provided that they are sized and shaped in a way that allows the port 10 to pass into the hole H in the bone B and be supported within the hole H and the bone B sufficiently so that the port does not exhibit substantial movement relative to the bone B, except during implantation and removal of the port 10.

This disclosure is provided to reveal a preferred embodiment of the invention and a best mode for practicing the invention. Having thus described the invention in this way, it should be apparent that various different modifications can be made to the preferred embodiment without departing from the scope and spirit of this invention disclosure. When structures are identified as a means to perform a function, the identification is intended to include all structures which can perform the function specified. When structures of this invention are identified as being coupled together, such language should be interpreted broadly to include the structures being coupled directly together or coupled together through intervening structures. Such coupling could be permanent or temporary and either in a rigid fashion or in a fashion which allows pivoting, sliding or other relative motion while still providing some form of attachment, unless specifically restricted.

What is claimed is:

1. An implantable port for providing vascular access, and which is supported by a bone, comprising in combination:
   a chamber;
   said chamber adapted to be placed into fluid communication with a vascular structure;
   a septum;
   said septum located adjacent at least one side of said chamber;
   said septum adapted to be penetrated by a needle and reseal after the needle is removed;
   a collar surrounding said septum;
   said collar adapted to hold said septum adjacent said chamber;

a bone engagement surface on said collar, said bone engagement surface adapted to be coupled to a bone to which the port is to be supported;

wherein said port includes a substantially rigid base separate from said collar, said base having said chamber located therein, said septum adapted to be interposed between said base and said collar, said collar adapted to be attached to said base with said septum trapped between said collar and said base with said septum overlying said chamber, said collar having an aperture, said aperture adapted to provide access for a needle to said septum on a side of said septum opposite said chamber;

said base and said collar together forming a body;

said chamber coupled to tubing having one end supported by said body with an interior of said tubing in fluid communication with said chamber;

said tubing extending from said chamber and adapted to access a vascular structure spaced from the bone to which said body is adapted to be supported;

said body having a face defining an end of said port closest to said aperture, said aperture accessed through said face; and said body having said bone engagement surface configured as a cylinder extending substantially perpendicularly from said face, said bone engagement surface including threads thereon adapted to threadably engage bone surrounding a hole formed in the bone for receipt of said port therein.

2. The port of claim 1 wherein said base exhibits a generally cylindrical form and said collar exhibits a generally cylindrical form with said base having male threads thereon complemental with female threads formed on said collar, such that said collar threads onto said base to secure said collar to said base with said septum between said collar and said base.

3. The implantable port of claim 1 wherein an end of said threads on said bone engagement surface closest to said face is located closer to said face than to an end of said body opposite said face.

4. The implantable port of claim 3 wherein said threads on said bone engagement surface extend to an end of said bone engagement surface adjacent said face.

5. The implantable port of claim 3 wherein said face includes a torque receiving facet adapted to receive torque from a torque applying tool to rotate said body relative to the bone in which said port is located.

6. A method for fixing a subcutaneous vascular access port at an implantation site, including the steps of:

providing an implantable access port having a body having a chamber therein; an aperture in the body, the aperture adapted to provide access into the chamber for a needle; a septum between the aperture and the chamber; and the chamber adapted to be coupled to a vascular structure with fluid communication between the chamber and the vascular structure;

attaching the port to a bone at the implantation site;

coupling the chamber to a vascular structure with fluid communication therebetween;

wherein said attaching step includes the step of forming a hole passing through the bone at the implantation site, the hole at least as large as an outer bone engagement surface of the body of the port;

locating the port within the hole with a majority of the port passing into the hole so that a majority of the port is below a surface of the bone in which the hole is formed; and wherein said coupling step includes routing a tube from a first end in communication with said chamber to a second end passing into a vascular structure separate from the bone, the tubing routed out of the bone on a side of the bone spaced from where the port enters the bone.

7. The method of claim 6 wherein said bone is a clavicle with the hole passing into a side of the clavicle which can be accessed by a needle passing through skin over the clavicle and then into the chamber through the septum.

8. The method of claim 6 including the further steps of:

providing threads on an outer surface of the body; and rotating the port with said threads engaging sides of the hole in the bone until the body of the port is at least partially affixed to the bone.

9. The method of claim 6 wherein said locating step includes the step of recessing the port substantially entirely below a surface of the bone and within the hole.

10. The method of claim 9 including the further step of positioning the aperture below the surface of the bone.

* * * * *